United States Patent
Oren et al.

(10) Patent No.: US 7,182,958 B1
(45) Date of Patent: *Feb. 27, 2007

(54) β-CARBOLINE PHARMACEUTICAL COMPOSITIONS

(75) Inventors: Peter L. Oren, Fishers, IN (US); Neil R. Anderson, West Lafayette, IN (US); Martha A. Kral, Indianapolis, IN (US)

(73) Assignee: Lilly Icos LLC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/031,464

(22) PCT Filed: Apr. 26, 2000

(86) PCT No.: PCT/US00/11130

§ 371 (c)(1),
(2), (4) Date: Apr. 29, 2002

(87) PCT Pub. No.: WO01/08686

PCT Pub. Date: Feb. 8, 2001

Related U.S. Application Data

(60) Provisional application No. 60/146,924, filed on Aug. 3, 1999.

(51) Int. Cl.
*A61K 9/20* (2006.01)
*A61K 9/48* (2006.01)
*A61K 9/64* (2006.01)

(52) U.S. Cl. ...... 424/464; 424/489; 424/451; 424/452; 424/455; 424/456; 514/250

(58) Field of Classification Search ...... 424/464, 424/451, 489; 514/182, 258
See application file for complete search history.

(56) References Cited

U.S. PATENT DOCUMENTS 4,721,709 A * 1/1988 Seth et al. ...... 514/221
6,943,166 B1 * 9/2005 Pullman et al. ...... 514/250

FOREIGN PATENT DOCUMENTS

| WO | WO 96/38131 | 12/1996 |
| WO | WO 97/03675 | 2/1997 |
| WO | WO 98/23270 | 6/1998 |

* cited by examiner

*Primary Examiner*—Lakshmi S. Channavajjala
(74) *Attorney, Agent, or Firm*—Marshall, Gerstein & Borun LLP

(57) ABSTRACT

Formulations containing a PDE5 inhibitor, a water-soluble diluent, a lubricant, a hydrophilic binder, a disintegrant, and optional microcrystalline cellulose and/or a wetting agent, and their use in treating sexual dysfunction, are disclosed.

32 Claims, No Drawings

β-CARBOLINE PHARMACEUTICAL COMPOSITIONS

CROSS-REFERENCE TO RELATED APPLICATIONS

This is the U.S. national phase application of International Application No. PCT/US00/11130, filed on Apr. 26, 2000, which claims the benefit of provisional patent application Ser. No. 60/146,924, filed Aug. 3, 1999.

FIELD OF THE INVENTION

This invention relates to the fields of pharmaceutical and organic chemistry involving β-carboline compounds which are useful in the treatment of the various medical indications where inhibition of type 5 cGMP-specific phosphodiesterase is desired. More particularly, β-carboline compounds are formulated in a manner providing uniform potency, and desirable stability and bioavailability characteristics.

BACKGROUND OF THE INVENTION

The biochemical, physiological, and clinical effects of cyclic guanosine 3',5'-monophosphate specific phosphodiesterase (cGMP-specific PDE) inhibitors suggest their utility in a variety of disease states in which modulation of smooth muscle, renal, hemostatic, inflammatory, and/or endocrine function is desired. Type 5 cGMP-specific phosphodiesterase (PDE5) is the major cGMP hydrolyzing enzyme in vascular smooth muscle, and its expression in penile corpus cavernosum has been reported (A. Taher et al., *J. Urol.*, 149, pp. 285A (1993)). Thus, PDE5 is an attractive target in the treatment of sexual dysfunction (K. J. Murray, *DN&P* 6(3), pp. 150–56 (1993)).

Daugan U.S. Pat. No. 5,859,006 discloses a class of β-carbolines, and pharmaceutical compositions thereof, which are useful in the treatment of conditions wherein inhibition of PDE5 is desired. Also, see PCT publication WO 97/03675 disclosing the use of such β-carbolines for the treatment of sexual dysfunction.

The poor solubility of many β-carbolines useful as PDE5 inhibitors has prompted the development of coprecipitate preparations, as disclosed in Butler U.S. Pat. No. 5,985,326. Briefly described, coprecipitates of β-carbolines with a polymer, e.g., hydroxypropyl methylcellulose phthalate, were prepared, then milled, mixed with excipients, and compressed into tablets for oral administration. However, studies revealed some difficulties in generating precisely reproducible lots of coprecipitate product, thereby making the use of coprecipitates less than ideal for pharmaceutical formulations.

In addition, clinical studies involving administration of tablets containing such a coprecipitate preliminarily revealed that maximum blood concentration of the β-carboline is achieved in 3 to 4 hours, with the average time for onset of a therapeutic effect as yet not precisely determined. When used for the treatment of sexual dysfunction, such as male erectile dysfunction or female arousal disorder, a more rapid attainment of maximum blood concentration, along with a greater prospect for rapid onset of therapeutic effect, is desired by patients, who prefer more immediate effects.

Accordingly, there is a continuing need in the art for oral dosage forms of β-carbolines, and pharmaceutical compositions thereof, useful in the treatment of conditions where inhibition of PDE5 is beneficial.

SUMMARY OF THE INVENTION

This invention provides pharmaceutical formulations comprising a compound of structural formula (I):

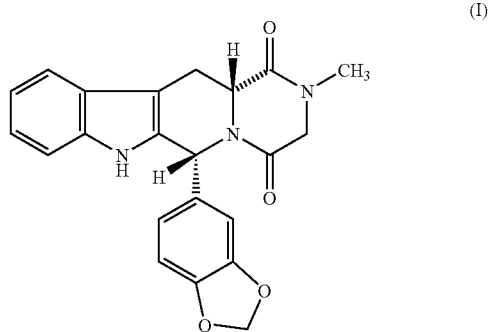

(I)

named (6R-trans)-6-(1,3-benzodioxol-5-yl)-2,3,6,7,12,12a-hexahydro-2-methylpyrazino-[1',2':1,6]pyrido[3,4-b]indole-1,4-dione, and alternatively named (6R,12aR)-2,3,6,7,12,12a-hexahydro-2-methyl-6-(3,4-methylenedioxyphenyl)pyrazino-[2',1':6,1]pyrido[3,4-b]indole-1,4-dione, and pharmaceutically acceptable salts and solvates thereof, wherein the compound preferably is provided as a free drug, in admixture with a diluent, a lubricant, a hydrophilic binder selected from the group consisting of a cellulose derivative, povidone, and a mixture thereof, a disintegrant selected from the group consisting of crospovidone, croscarmellose sodium, and a mixture thereof, and, optionally, microcrystalline cellulose and/or a wetting agent. Optionally, the formulation additionally comprises a second diluent.

A most preferred pharmaceutical formulation of the present invention comprises: (a) about 1 to about 5, and more preferably about 2 to about 4, weight percent of the compound of structural formula (I), provided as free drug; (b) about 50 to about 85 weight percent, and preferably about 50 to about 75 percent, lactose; (c) about 0.25 to about 2 weight percent magnesium stearate; (d) about 1 to about 5 weight percent hydroxypropylcellulose; (e) about 3 to about 15 weight percent croscarmellose sodium; (f) 0 to about 40 weight percent microcrystalline cellulose; and (g) 0 to about 5 weight percent sodium lauryl sulfate.

The present invention further relates to the use of such formulations for treatment of sexual dysfunction, e.g., male erectile dysfunction and female arousal disorder. The formulations can be administered orally as a compressed tablet or as dry, free-flowing particles encapsulated in a hard shell, for example, a gelatin shell.

DETAILED DESCRIPTION OF THE INVENTION

For purposes of the invention disclosed and claimed herein, the following terms and abbreviations have the following meanings.

The term "treatment" is defined to include preventing, lowering, stopping, or reversing the progression or severity of a condition or symptom being treated. As such, the present invention includes both medical therapeutic and/or prophylactic administration, as appropriate.

The term "effective amount" is an amount of a pharmaceutical formulation that is effective in treating the desired condition or symptom. An effective amount of the compound of structural formula (I) to treat sexual dysfunction in a male is an amount sufficient to provide and sustain an erection capable of penetrating his partner. An effective amount of the compound of structural formula (I) to treat female sexual dysfunction, particularly female arousal disorder, is an amount sufficient to enhance the patient's ability to achieve or sustain an aroused state.

The term "free drug" refers to solid particles consisting essentially of the compound of structural formula (I), as opposed to the compound intimately embedded in a polymeric coprecipitate.

The term "lubricant" refers to pharmaceutically acceptable agents that are commonly used in the art as lubricants or glidants in the preparation of solid pharmaceutical formulations. Representative lubricants include, but are not limited to, agents such as talc, magnesium stearate, calcium stearate, stearic acid, colloidal silicon dioxide, calcium silicate, a starch, mineral oil, a wax, glyceryl behenate, a polyethylene glycol, sodium benzoate, sodium acetate, sodium stearyl fumarate, and hydrogenated vegetable oils. Preferably, the lubricant is selected from the group consisting of magnesium stearate, sodium stearyl fumarate, and stearic acid. Most preferably, the lubricant is magnesium stearate.

The term "solvate" refers one or more molecules of a solute associated with a molecule of a compound, such as the compound of structural formula (I) associated with a molecule of water or acetic acid.

The term "solid oral dosage form" is used in a general sense to refer to solid pharmaceutical products administered orally. Solid oral dosage forms are recognized by those skilled in the art to include such forms as tablets and capsules, for example.

The term "water-soluble diluent" refers to compounds typically used in the formulation of pharmaceuticals to impart bulk for the manufacture of a tablet of practical size. Water-soluble diluents include, but are not limited to, sugars (including lactose, sucrose, and dextrose), polysaccharides (including dextrates and maltodextrin), polyols (including mannitol, xylitol, and sorbitol), and cyclodextrins.

The term "wetting agent" refers to anionic, cationic, and nonionic surfactants. Nonlimiting, representative wetting agents include sodium lauryl sulfate, docusate sodium (i.e., bis(2-ethyl-hexyl)sodium sulfosuccinate), ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides and ethoxylated derivatives thereof, and diglycerides and ethoxylated derivatives thereof. Preferably the surfactant is sodium lauryl sulfate or a polyoxyethylene sorbitan fatty acid ester, particularly polysorbate 80.

The nomenclature describing particle size is commonly referred to herein as the "d90." A d90 of 40 means that at least 90% of the particles have a particle size less than 40 microns.

As previously stated, the present invention provides pharmaceutical formulations containing the compound of structural formula (I), as disclosed in Daugan U.S. Pat. No. 5,859,006, and pharmaceutically acceptable solvates thereof. A preferred solvent suitable to prepare the compound of structural formula (I) includes acetic acid.

Applicants have found that dosage uniformity, stability, and bioavailability are enhanced by formulating (6R-trans)-6-(1,3-benzodioxol-5-yl)-2,3,6,7,12,12a-hexahydro-2-methylpyrazino-[1',2':1,6]pyrido[3,4-b]indole-1,4-dione (i.e., the compound of structural formula (I), also referred to herein as Compound A), as the active compound with a particular combination of pharmaceutical excipients. The formulations of present invention comprise mixtures of the active compound with a water-soluble diluent, a lubricant, a hydrophilic binder, croscarmellose sodium or crospovidone as a disintegrant, and, optionally, microcrystalline cellulose and/or a wetting agent.

The total amount of active Compound A in the pharmaceutical formulations is about 0.1% to about 45%, preferably about 0.5% to about 10%, by weight of the formulation. In more preferred embodiments, the active compound is present in an amount of about 1% to about 4%, and most preferably, about 2% to about 4%, by weight of the formulation. The compound of structural formula (I) can be made according to established procedures, such as those disclosed in Daugan U.S. Pat. No. 5,859,006, incorporated herein by reference.

The particle size of the active compound also has been found to enhance the bioavailability and handling of the present formulations. Thus, the particle size of the compound of structural formula (I) prior to formulation is controlled by milling the raw compound (as a crystal, amorphous precipitate, or mixture thereof) such that at least 90% of the particles have a particle size of less than about 40 microns (d90=40), and preferably less than about 30 microns. More preferably, at least 90% of the particles have a particle size of less than about 25 microns, still more preferably, less than about 15 microns, and most preferably, less than about 10 microns.

Methods for determining the size of particles are well known in the art. The following nonlimiting method disclosed in U.S. Pat. No. 4,605,517, incorporated herein by reference, can be employed. In particular, the laser scattering particle size distribution analysis is effected on a small sample of the reduced material which is suspended in approximately 180 ml of dispersant solution. The sample is added to the dispersant until an acceptable level of laser light obscuration is achieved, at which point the particle size distribution is measured. Prior to sample suspension, a dispersant solution is prepared by preparing a solution of 0.1% SPAN 80 (sorbitan oleate) in cyclohexane which is presaturated with the compound. The dispersant solution is filtered through a 0.2 micron microporous membrane filter to provide the necessary particle-free suspending dispersant. Triplicate measurements are effected as a minimum (a) to produce more reliable measurements, and (b) to check the equivalent sampling of the suspended material. The results are automatically recorded and displayed graphically to give a cumulative % undersize vs. diameter, and a frequency percentage vs. diameter for the sample. From this data, the median equivalent spherical volume diameter value and d90 are derived (90% undersize value) together with the standard deviation of the distribution calculated as above.

A water-soluble diluent is present in the formulation in an amount sufficient to provide adequate bulk to the formulation, and to effect tablet manufacture. A preferred water-soluble diluent is lactose, present in an amount of about 50% to about 85%, and preferably, about 50% to about 75%, by weight.

A hydrophilic binder is provided in an amount sufficient to act as an adhesive to hold Compound A and excipients together in a tablet. A hydrophilic binder also is present in a powder formulation introduced into a hard gelatin shell. In dry powder formulations, the hydrophilic binder facilitates powder manufacture and handling, and enhances stability of the active compound.

A preferred hydrophilic binder is a cellulose derivatives, including, for example, hydroxypropylcellulose and hydroxypropyl methylcellulose. Another nonlimiting hydrophilic binder is povidone. Preferably, the amount of hydrophilic binder present in the formulation is about 1% to about 5%, by weight of the formulation.

While binders such as povidone provide suitable adhesive characteristics, it has been found that the binder is important with respect to the stability of the β-carboline compound. Hydroxypropylcellulose and hydroxypropyl methylcellulose offer acceptable adhesion, while avoiding the oxidative instability attributed to povidone, and thus are preferred binders.

The croscarmellose sodium and crospovidone promote disintegration of the formulation, and especially a tablet dosage form, after administration and upon contact with water. Croscarmellose sodium and crospovidone are particularly advantageous when used in an amount of about 3% to about 15%, and especially about 3% to about 10%, by weight of the formulation. Croscarmellose sodium, also known as carboxymethylcellulose sodium crosslinked, is the preferred disintegrant. Crospovidone is crosslinked povidone.

A lubricant is provided in an amount sufficient to reduce die wall friction during compression of the formulation into tablets. Preferably, the lubricant is magnesium stearate, present in an amount of about 0.25% to about 2.0%, by weight of the formulation. A lubricant also facilitates handling of the dry powder form of the formulation.

Microcrystalline cellulose is present at 0 to about 40% by weight in the present compositions. Microcrystalline cellulose can serve multiple functions in the formulation, e.g., a disintegrant and/or a second diluent in addition to the water-soluble diluent.

If desired, wetting agents are provided in an amount sufficient to decrease interfacial tension between drug particles and the dissolving medium (e.g., gastric fluids), and thereby enhance drug dissolution and absorption. Preferably, the surfactant is sodium lauryl sulfate or a polyoxyethylene sorbitan fatty acid ester, particularly polysorbate 80, in an amount of 0% to about 5%, and preferably about 0.1% to about 5%, by weight of the formulation.

Additional optional ingredients, such as coloring or flavoring agents, can be incorporated into the formulation in an amount sufficient to perform their intended function without adversely affecting either the powder formulation or tablets manufactured using the formulation.

In preferred embodiments, the relative percentage of formulation components (by weight) is as follows:

|  | Quantity (% by weight) |
|---|---|
| Compound of Structural Formula (I) | 1 to 4 |
| Lactose (diluent) | 50 to 85 |
| Hydrophilic Binder | 1 to 5 |
| Croscarmellose Sodium (disintegrant) | 3 to 15 |
| Sodium Lauryl Sulfate (wetting agent) | 0 to 5 |
| Microcrystalline Cellulose (diluent/disintegrant) | 0 to 40 |
| Magnesium Stearate (lubricant) | 0.25 to 2 |

The formulations of the present invention can be prepared by a variety of techniques recognized in the art. Such techniques include, for example, wet granulation followed by drying, milling and compression into tablets with or without film coating, dry granulation followed by milling, compression into tablets with or without film coating, dry blending followed by compression into tablets, with or with film coating, molded tablets, wet granulation, dried and filled into gelatin capsules, dry blend filled into gelatin capsules, or suspension or solution filled into gelatin capsules. Generally, the compositions have identifying marks which are debossed or imprinted on the surface.

In addition to improved dissolution and in vivo absorption, another important physical property is stability. The present invention provides formulations with improved stability over prior formulations.

The specific dose of Compound A administered according to the present invention is determined by the particular circumstances surrounding the case including, for example, the route of administration, the dosage form, the condition of the patient, and the pathological condition being treated. A typical daily dose contains a dosage level of about 1 to about 20 mg/day of the compound of structural formula (I). Preferred daily doses generally are about 1 to about 10 mg/day, particularly about 5 mg or about 10 mg tablets or capsules, administered once per day. The most preferred dosage form is a tablet. Multiple doses can be taken to achieve a total dose of up to 20 mg/day of the compound of structural formula (I). The selection of dose level is decided by the attending physician.

One useful dosage form is a hard capsule comprising a powdered form of the formulation in a hard, soluble shell. In accordance with the present invention, the hard capsules are a solid dosage form in which dry, free-flowing particles of the drug formulation are filled in a hard container or shell comprising a gelatin, a starch, or other capsule materials well known to persons skilled in the art. Gelatin possesses unique properties which make gelatin the primary material for the manufacture of hard capsule shells. Another example of a useful capsule material is potato starch.

Hard capsules provide some advantages over other solid dosage forms, such as tablets. For example, many patients prefer capsules because capsules are easier to swallow. Thus, capsule forms of a drug often are made available in addition to tablet forms.

A hard capsule has a hard shell completely surrounding the dry formulation. Typically, the dry drug formulation is added to a first section of the capsule, then a second section of the capsule is slipped over an open end of the first section to surround the drug formulation. The size and shape of the hard shell can vary, but typically is cylindrical with rounded ends. The size of the capsule is related to the dose level of the drug encapsulated by the shell, and to the particular drug formulation.

A hard capsule oral dosage form typically is prepared such that the shell ruptures or dissolves to release the enclosed drug formulation within five to ten minutes after ingestion. Manufacture of the hard shell, and the capsules, is performed in accordance with methods well known in the art.

The following formulation examples are illustrative only, and are not intended to limit the scope of the present invention. In particular, the following examples are directed to tablets, but the identical formulations, in a dry free-flowing particulate or powder form, can be used in a hard capsule.

EXAMPLE 1

Lot 1 of Compound A was made using a 12 inch pancake style jet mill fed at a rate of 28 to 30 kg/hour with sufficient grind pressure to produce material having a d90 of 4 microns.

The following formula was used to prepare the finished dosage form, i.e., a tablet providing 10.0 mg of Compound A from Lot 1 material.

| Ingredient | Quantity (mg) |
|---|---|
| Granulation | |
| Compound A (d90 of 4) | 10.0 |
| Lactose Monohydrate | 153.8 |
| Lactose Monohydrate (spray dried) | 25.0 |
| Hydroxypropyl Cellulose | 4.0 |
| Croscarmellose Sodium | 9.0 |
| Hydroxypropyl Cellulose (EF) | 1.75 |
| Sodium Lauryl Sulfate | 0.7 |
| Outside Powders | |
| Microcrystalline Cellulose (Granular-102) | 37.5 |
| Croscarmellose Sodium | 7.0 |
| Magnesium Stearate (vegetable) | 1.25 |
| Total | 250 mg |

Purified Water, USP was used in the manufacture of the tablets. The water was removed during processing, and minimal levels remained in the finished product.

The tablets were manufactured using a wet granulation process. A step by step description of the process follows: Compound A and excipients were security sieved. The selective PDE5 inhibitor (i.e., Compound A) was dry blended with lactose monohydrate (spray dried), hydroxypropyl cellulose, croscarmellulose sodium, and lactose monohydrate. The resulting powder blend was granulated with an aqueous solution of hydroxypropyl cellulose and sodium lauryl sulfate using a Powrex or other suitable high shear granulator. Additional water can be added to reach the desired endpoint. A mill can be used to delump the wet granulation and facilitate drying. The wet granulation was dried using either a fluid bed dryer or a drying oven. After the material was dried, it can be sized to eliminate large agglomerates.

Microcrystalline cellulose, croscarmellose sodium, and magnesium stearate were security sieved and added to the dry sized granules. These excipients and the dry granulation were mixed until uniform, using a tumble bin, ribbon mixer, or other suitable mixing equipment. The mixing process can be separated into two phases: (a) the microcrystalline cellulose, croscarmellose sodium and the dried granulation are added to the mixer and blended, followed by (b) the addition of the magnesium stearate to this granulation and a second mixing phase.

The mixed granulation then was compressed into tablets using a rotary compression machine. The core tablets, if desired, can be film coated with an aqueous suspension of the appropriate color mixture in a coating pan (e.g., Accela Cota). The coated tablets can be lightly dusted with talc to improve tablet handling characteristics.

The tablets can be filled into plastic containers (30 tablets/ container) and accompanied by a package insert describing the safety and efficacy of the compound.

EXAMPLE 2

By analogous procedures the following formula was used to prepare a finished dosage form of a tablet providing 5 mg of Compound A of Lot 1.

| Ingredient | Quantity (mg) |
|---|---|
| Granulation | |
| Compound A (d90 of 4) | 5.00 |
| Lactose Monohydrate | 109.655 |
| Lactose Monohydrate (spray dried) | 17.50 |
| Hydroxypropyl Cellulose | 2.80 |
| Croscarmellose Sodium | 6.30 |
| Hydroxypropyl Cellulose (EF) | 1.225 |
| Sodium Lauryl Sulfate | 0.49 |
| Outside Powders | |
| Microcrystalline Cellulose (Granular-102) | 26.25 |
| Croscarmellose Sodium | 4.90 |
| Magnesium Stearate (vegetable) | 0.88 |
| Total | 175 mg |

EXAMPLE 3

By analogous procedures the following formula was used to prepare a finished dosage form of a tablet providing 2.5 mg of Compound A.

| Ingredient | Quantity (mg) |
|---|---|
| Granulation | |
| Compound A | 2.50 |
| Lactose Monohydrate | 79.395 |
| Lactose Monohydrate (spray dried) | 12.50 |
| Hydroxypropyl Cellulose | 2.00 |
| Croscarmellose Sodium | 4.50 |
| Hydroxypropyl Cellulose (EF) | 0.875 |
| Sodium Lauryl Sulfate | 0.35 |
| Outside Powders | |
| Microcrystalline Cellulose (Granular-102) | 18.75 |
| Croscarmellose Sodium | 3.5 |
| Magnesium Stearate (vegetable) | 0.63 |
| Total | 125 mg |

EXAMPLE 4

By analogous procedures the following formula was used to prepare a finished dosage form of a tablet providing 10 mg of Compound A, without a film coating.

| Ingredient | Quantity (mg) |
|---|---|
| Granulation | |
| Compound A | 10.00 |
| Lactose Monohydrate | 153.80 |
| Lactose Monohydrate (spray dried) | 25.00 |
| Hydroxypropyl Cellulose | 4.00 |
| Croscarmellose Sodium | 9.0 |
| Hydroxypropyl Cellulose (EF) | 1.75 |
| Sodium Lauryl Sulfate | 0.70 |

-continued

| Ingredient | Quantity (mg) |
|---|---|
| Outside Powders | |
| Microcrystalline Cellulose (Granular-102) | 37.50 |
| Croscarmellose Sodium | 7.00 |
| Stearic Acid (powder) | 3.75 |
| Total | 252.5 mg |

EXAMPLE 5

By analogous procedures the following formula was used to prepare a finished dosage form of a tablet providing 10 mg of Compound A, without a film coating.

| Ingredient | Quantity (mg) |
|---|---|
| Granulation | |
| Compound A | 10.00 |
| Lactose Monohydrate | 153.80 |
| Mannitol | 25.00 |
| Hydroxypropyl Cellulose | 4.00 |
| Croscarmellose Sodium | 9.00 |
| Hydroxypropyl Cellulose (EF) | 1.75 |
| Sodium Lauryl Sulfate | 0.70 |
| Outside Powders | |
| Microcrystalline Cellulose (Granular-102) | 37.50 |
| Croscarmellose Sodium | 7.00 |
| Magnesium Stearate (vegetable) | 1.25 |
| Total | 250 mg |

EXAMPLE 6

By analogous procedures the following formula was used to prepare a finished dosage form of a tablet providing 10 mg of Compound A, without a film coating.

| Ingredient | Quantity (mg) |
|---|---|
| Granulation | |
| Compound A | 10.00 |
| Lactose Monohydrate | 153.80 |
| Lactose Monohydrate (spray dried) | 25.00 |
| Povidone | 4.00 |
| Croscarmellose Sodium | 9.00 |
| Povidone | 1.75 |
| Sodium Lauryl Sulfate | 0.70 |
| Outside Powders | |
| Microcrystalline Cellulose (Granular-102) | 37.50 |
| Croscarmellose Sodium | 7.00 |
| Magnesium Stearate (vegetable) | 1.25 |
| Total | 250 mg |

EXAMPLE 7

By analogous procedures the following formula was used to prepare a finished dosage form of a tablet providing 10 mg of Compound A, without a film coating.

| Ingredient | Quantity (mg) |
|---|---|
| Granulation | |
| Compound A | 10.00 |
| Lactose Monohydrate | 153.80 |
| Lactose Monohydrate (spray dried) | 25.00 |
| Povidone | 4.00 |
| Croscarmellose Sodium | 9.00 |
| Povidone | 1.75 |
| Polysorbate 80 | 0.70 |
| Outside Powders | |
| Microcrystalline Cellulose (Granular-102) | 37.50 |
| Croscarmellose Sodium | 7.00 |
| Magnesium Stearate (vegetable) | 1.25 |
| Total | 250 mg |

EXAMPLE 8

By analogous procedures the following formula was used to prepare a finished dosage form of a tablet providing 10 mg of Compound A, without a film coating.

| Ingredient | Quantity (mg) |
|---|---|
| Granulation | |
| Compound A | 10.00 |
| Lactose Monohydrate | 157.80 |
| Lactose Monohydrate (spray dried) | 25.00 |
| Croscarmellose Sodium | 9.00 |
| Hydroxypropyl Methylcellulose | 1.75 |
| Sodium Lauryl Sulfate | 0.70 |
| Outside Powders | |
| Microcrystalline Cellulose (Granular-102) | 37.50 |
| Croscarmellose Sodium | 7.00 |
| Magnesium Stearate (vegetable) | 1.25 |
| Total | 250 mg |

EXAMPLE 9

By analogous procedures the following formula was used to prepare a finished dosage form of a tablet providing 10 mg of Compound A, without a film coating.

| Ingredient | Quantity (mg) |
|---|---|
| Granulation | |
| Compound A | 10.00 |
| Lactose Monohydrate | 153.80 |
| Sucrose | 25.00 |
| Hydroxypropyl Cellulose | 4.00 |
| Croscarmellose Sodium | 9.00 |
| Hydroxypropyl Cellulose (EF) | 1.75 |
| Sodium Lauryl Sulfate | 0.70 |

-continued

| Ingredient | Quantity (mg) |
| --- | --- |
| Outside Powders | |
| Microcrystalline Cellulose (Granular-102) | 37.50 |
| Croscarmellose Sodium | 7.00 |
| Magnesium Stearate (vegetable) | 1.25 |
| Total | 250 mg |

EXAMPLE 10

By analogous procedures the following formula was used to prepare a finished dosage form of a tablet providing 10 mg of Compound A, without a film coating.

| Ingredient | Quantity (mg) |
| --- | --- |
| Granulation | |
| Compound A | 10.00 |
| Lactose Monohydrate | 153.80 |
| Lactose Monohydrate (spray dried) | 25.00 |
| Hydroxypropyl Cellulose | 4.00 |
| Croscarmellose Sodium | 9.00 |
| Hydroxypropyl Cellulose (EF) | 1.75 |
| Sodium Lauryl Sulfate | 0.70 |
| Outside Powders | |
| Microcrystalline Cellulose (Granular-102) | 37.50 |
| Croscarmellose Sodium | 7.00 |
| Sodium Stearyl Fumarate | 1.25 |
| Total | 250 mg |

EXAMPLE 11

By analogous procedures the following formula was used to prepare a finished dosage form of a tablet providing 10 mg of Compound A, without a film coating.

| Ingredient | Quantity (mg) |
| --- | --- |
| Granulation | |
| Compound A | 10.00 |
| Lactose Monohydrate | 153.80 |
| Lactose Monohydrate (spray dried) | 25.00 |
| Hydroxypropyl Cellulose | 4.00 |
| Croscarmellose Sodium | 9.00 |
| Hydroxypropyl Cellulose (EF) | 1.75 |
| Sodium Lauryl Sulfate | 0.70 |
| Outside Powders | |
| Croscarmellose Sodium | 7.00 |
| Magnesium Stearate (vegetable) | 1.25 |
| Total | 212.50 mg |

EXAMPLE 12

By analogous procedures the following formula was used to prepare a finished dosage form of a tablet providing 10 mg of Compound A, without a film coating.

| Ingredient | Quantity (mg) |
| --- | --- |
| Granulation | |
| Compound A | 10.00 |
| Lactose Monohydrate | 153.80 |
| Lactose Monohydrate (spray dried) | 25.00 |
| Hydroxypropyl Cellulose | 4.00 |
| Crospovidone | 27.00 |
| Hydroxypropyl Cellulose (EF) | 1.75 |
| Sodium Lauryl Sulfate | 0.70 |
| Outside Powders | |
| Microcrystalline Cellulose (Granular-102) | 19.50 |
| Crospovidone | 7.00 |
| Magnesium Stearate (vegetable) | 1.25 |
| Total | 250 mg |

EXAMPLE 13

By analogous procedures the following formula was used to prepare a finished dosage form of a tablet providing 10 mg of Compound A, without a film coating.

| Ingredient | mg/tablet |
| --- | --- |
| Granulation | |
| Compound A | 10.00 |
| Lactose Monohydrate | 154.50 |
| Lactose Monohydrate (spray dried) | 25.00 |
| Hydroxypropyl Cellulose | 4.00 |
| Croscarmellose Sodium | 9.00 |
| Hydroxypropyl Cellulose (EF) | 1.75 |
| Outside Powders | |
| Microcrystalline Cellulose (Granular-102) | 37.50 |
| Croscarmellose Sodium | 7.00 |
| Magnesium Stearate | 1.75 |
| Total | 250.0 mg |

The principles, preferred embodiments, and modes of operation of the present invention have been described in the foregoing specification. The invention that is intended to be protected herein, however, is not construed to be limited to the particular forms disclosed, because they are illustrative rather than restrictive. Variations and changes may be made by those skilled in the art without departing from the spirit of the invention.

What is claimed is:

1. A pharmaceutical formulation comprising an active compound having the structural formula

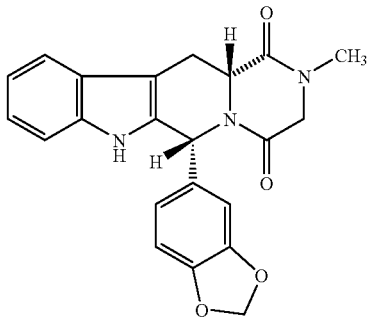

wherein said compound is provided as free drug comprising particles wherein at least 90% of the particles of the said compound have a particle size of less than about 40 microns; about 50% to about 85%, by weight, of a water-soluble diluent; a lubricant; a hydrophilic binder selected from the group consisting of a cellulose derivative, povidone, and a mixture thereof; and a disintegrant selected from the group consisting of croscarmellose sodium, crospovidone, and a mixture thereof.

2. The formulation of claim 1 further comprising microcrystalline cellulose.

3. The formulation of claim 1 further comprising a wetting agent.

4. The formulation of claim 1 wherein the active compound is present in an amount of about 0.5% to about 10% by weight.

5. The formulation of claim 1 wherein the water-soluble diluent is selected from the group consisting of a sugar, a polysaccharide, a polyol, a cyclodextrin, and mixtures thereof.

6. The formulation of claim 1 wherein the water-soluble diluent is selected from the group consisting of lactose, sucrose, dextrose, a dextrate, a maltodextrin, mannitol, xylitol, sorbitol, a cyclodextrin, and mixtures thereof.

7. The formulation of claim 1 wherein the lubricant is present in an amount of about 0.25% to about 2% by weight.

8. The formulation of claim 1 wherein the lubricant is selected from the group consisting of talc, magnesium stearate, calcium stearate, stearic acid, colloidal silicon dioxide, calcium silicate, a starch, mineral oil, a wax, glyceryl behenate, a polyethylene glycol, sodium benzoate, sodium acetate, sodium stearyl fumarate, hydrogenated vegetable oils, and mixtures thereof.

9. The formulation of claim 1 wherein the hydrophilic binder is present in an amount of about 1% to about 5% by weight.

10. The formulation of claim 1 wherein the cellulose derivative is selected from the group consisting of hydroxypropylcellulose, hydroxypropyl methylcellulose, and mixtures thereof.

11. The formulation of claim 1 wherein the disintegrant is present in an amount of about 3% to about 10% by weight.

12. The formulation of claim 2 wherein the microcrystalline cellulose is present in an amount of about 5% to about 40% by weight.

13. The formulation of claim 3 wherein the wetting agent is present in an amount of about 0.1% to about 5% by weight.

14. The formulation of claim 13 wherein the wetting agent is selected from the group consisting of sodium lauryl sulfate, docusate sodium, ethoxylated castor oil, a polyglycolyzed glyceride, an acetylated monoglyceride, a sorbitan fatty acid ester, a poloxamer, a polyoxyethylene sorbitan fatty acid ester, a polyoxyethylene, a monoglyceride and ethoxylated derivatives thereof, a diglyceride and ethoxylated derivatives thereof, and mixtures thereof.

15. The formulation of claim 14 wherein the wetting agent is selected from the group consisting of sodium lauryl sulfate, polysorbate 80, and a mixture thereof.

16. The formulation of claim 1 wherein the active compound is provided as particles of a free drug wherein at least 90% of the particles have a particle size less than about 10 microns.

17. The formulation of claim 1 comprising:
  (a) about 1% to about 4% by weight of the active compound;
  (b) about 50% to about 75% by weight lactose;
  (c) about 0.25% to about 2% by weight magnesium stearate;
  (d) about 1% to about 5% by weight hydroxypropyl cellulose; and
  (e) about 3% to about 10% by weight croscarmellose sodium.

18. The formulation of claim 16 further comprising about 5% to about 40% by weight microcrystalline cellulose.

19. The formulation of claim 16 further comprising about 0.1% to about 5% by weight sodium lauryl sulfate.

20. A tablet comprising the formulation of claim 1 wherein the active compound is present in an amount of about 1 to about 20 mg per tablet.

21. A tablet comprising the formulation of claim 1 wherein the active compound is present in an amount of about 5 to about 15 mg per tablet.

22. A tablet comprising the formulation of claim 1 wherein the active compound is present in an amount of about 5 mg per tablet.

23. A capsule comprising a hard shell encasing the formulation of claim 1 as dry, free-flowing particles, wherein the active compound is present in an amount of about 1 to about 20 mg per capsule.

24. The formulation of claim 1 wherein the active compound is provided as particles of a free drug wherein at least 90% of the particles have a particle size less than about 30 microns.

25. The formulation of claim 1 wherein the active compound is provided as particles of a free drug wherein at least 90% of the particles have a particle size less than about 25 microns.

26. The formulation of claim 1 wherein the active compound is provided as particles of a free drug wherein at least 90% of the particles have a particle size less than about 15 microns.

27. A tablet comprising the formulation of claim 1 wherein the active compound is present in an amount of about 10 mg per tablet.

28. A tablet comprising the formulation of claim 1 wherein the active compound is present in an amount of about 1 to about 5 mg per tablet.

29. A tablet comprising the formulation of claim 1 wherein the active compound is present in an amount of about 2.5 mg per tablet.

30. A tablet comprising the formulation of claim 1 wherein the active compound is present in an amount of about 20 mg per tablet.

31. A method of treating sexual dysfunction in a patient in need thereof comprising administering to the patient an effective amount of a formulation or a tablet according to of any one of claims 1 through 4, 5 through 15, 16 through 23, or 28 through 30.

32. The method of claim 31 wherein the sexual dysfunction is male erectile dysfunction.

* * * * *

UNITED STATES PATENT AND TRADEMARK OFFICE
CERTIFICATE OF CORRECTION

PATENT NO. : 7,182,958 B1
APPLICATION NO. : 10/031464
DATED : February 27, 2007
INVENTOR(S) : Peter L. Oren et al.

It is certified that error appears in the above-identified patent and that said Letters Patent is hereby corrected as shown below:

On the Title Page:

Item (73), "Lilly Icos LLC." should be -- Lilly ICOS LLC --.

In the Specification:

Column 5, line 4, "derivatives" should be -- derivative --.

Column 7, line 38, "croscarmellulose" should be -- croscarmellose --.

Signed and Sealed this

Eighteenth Day of December, 2007

JON W. DUDAS
*Director of the United States Patent and Trademark Office*